United States Patent [19]

Natori et al.

[11] Patent Number: 5,106,735
[45] Date of Patent: Apr. 21, 1992

[54] **CLONING OF A DNA SEQUENCE ENCODING A *SARCOPHAGA PEREGRINA* ANTIBACTERIAL POLYPEPTIDE PRECURSOR**

[75] Inventors: Shunji Natori, Tone; Haruo Takahashi, Aichi; Kenichi Tanaka, Aichi; Takahiko Mitani, Aichi; Masayasu Kurono, Aichi; Kiichi Sawai, Aichi, all of Japan

[73] Assignee: Sanwa Kagaku Kenkyusho Co., Ltd., Aichi, Japan

[21] Appl. No.: 223,304

[22] Filed: Jul. 25, 1988

[30] Foreign Application Priority Data

Aug. 20, 1987 [JP] Japan .................. 62-205164

[51] Int. Cl.⁵ .................. C12P 19/34; C12Q 1/68; C12N 15/00; C12N 1/21; C12N 15/70; C07H 15/12; A61K 37/02
[52] U.S. Cl. .................. 435/91; 435/6; 435/172.3; 435/252.3; 435/252.33; 435/320.1; 536/27; 530/300; 935/18; 935/29; 935/41; 935/56; 935/72; 935/73
[58] Field of Search .................. 435/69.1, 71.2, 91, 435/172.3, 252.33, 320, 6, 252.3; 530/350, 300; 536/27; 535/18, 27, 41, 56, 61, 73, 78

[56] References Cited

PUBLICATIONS

Matsumoto et al., Biochem. J., vol. 239, pp. 717–722, (1986).
Suggs et al., Proc. Natl. Acad. Sci., USA, vol. 78, pp. 6613–6617, (1981).
Euro. J. Biochem., 106, 7–16(1980), Insect Immunity. Purification and Properties of Three Induible Bactericidal Proteins from Hemolymph of Immunized Pupae of *Hyalophora cecropia*.

*Primary Examiner*—Joan Ellis
*Attorney, Agent, or Firm*—Armstrong, Nikaido, Marmelstein, Kubovcik & Murray

[57] ABSTRACT

A cloned single-strand DNA comprising nucleotide sequence which encodes an antibacterial polypeptide precursor, a cloned double-strand DNA consisting of the single-strand DNA and its complementary single-strand DNA, a DNA fragment of the single- or double-strand DNA, a process for the preparation thereof, and a plasmid, in which the double-strand DNA or its fragment is inserted.

4 Claims, 3 Drawing Sheets

FIG. 2

```
      -90        -80        -70        -60        -50        -40        -30        -20        -10         -1
5'----ATCAGTGTCTTATAGACTTAGTCAAATATCACAACAAACTAAATTGTTTTAACAAAAGTAATTAAAAAAAATAATTAAAAACCAAGAAAA 1         10         20         30         40         50         60         70         80         90
      ATGAAATCCTTCATCGTACTCGCTGTTACCTTGCTTGCTCTGGCTGCCTTCTTTATGGGTCAATCCGTAGCCTCGCTGCAGCTGCTGAG
      MetLysSerPheIleValLeuAlaValThrLeuLeuAlaLeuAlaAlaPhePheMetGlyGlnSerValAlaSerProAlaAlaAlaGlu
       1                    10                   20                                      30

100        110        120        130        140        150        160        170        180
      GAATCTAAATTGTTGATGGTTTGCATGCCTTAAAAACTATTGAACCGGAATTGCATGCCGCTACAAGAGAGCCACTTGCGATTATTG
      GluSerLysPheValAspGlyLeuHisAlaLeuLysThrIleGluProGluLeuHisGlyArgTyrLysArgAlaThrCysAspLeuLeu
                    40                   50                                      60

190        200        210        220        230        240        250        260        270
      AGTGGCACTGGCATCAATCACTCGGCTTGTGCTGCCCATTGCTGTTGAGAGAAAAATCGTGGGGCTATTGCAAATGGCAAAGCTGTCTGC
      SerGlyThrGlyIleAsnHisSerAlaCysAlaAlaHisCysLeuLeuArgGlyAsnArgGlyGlyTyrCysAsnGlyLysAlaValCys
                    70                   80                                      90

280        290        300        310        320        330        340        350
      GTATGTGCGCAATAAGAAATCTTATTTTACATAGAAAATTATAATTAATAAAGTGATCACTTAAGTATTAACAAAC---3'
      ValCysArgAsn***
```

CLONING OF A DNA SEQUENCE ENCODING A *SARCOPHAGA PEREGRINA* ANTIBACTERIAL POLYPEPTIDE PRECURSOR

BACKGROUND OF THE INVENTION

1. Field of the Invention

The present invention relates to a cloned single-stranded DNA comprising a nucleotide sequence which encodes an antibacterial polypeptide precursor, a cloned double-stranded DNA consisting of the single-stranded DNA and its complementary single-stranded DNA, a DNA fragment of the single- or double-stranded DNA, a process for the preparation thereof, and a plasmid, in which the double-strand DNA or its fragment is inserted.

2. Related Arts

It has been known that a certain antibacterial substance will appear in a body fluid, when a vaccine is inoculated to an invertebrate such as insecta ["Eur. J. Biochem." Vol. 106, page 7, (1980)].

One of the present inventors has found that the flesh fly (*Sarcophaga peregrina*) produces a certain antibacterial polypeptide in its body fluid, when a larva of the insect is injured in its body wall, the polypeptide being separated and purified to investigate its physicochemical properties [see Jap. Pat. Nos. 59-13730 (A) published Jan. 24, 1984 and 61-122299 (A) published June 10, 1986].

Further, the inventor has found several antibacterial polypeptides from culture supernatant of a cell line (named as—NIH-Sape-4—) established from *Sarcophaga peregrina* embryo, one of the polypeptides being purified to investigate its physicochemical properties and structure and to find that the polypeptide consists of 40 amino acids with 6 cysteine residues in its molecular structure (Jap. Pat. Appln. Nos. 14806/1987 and 14807/1987 which correspond to U.S. Pat. Appln. Ser. Nos. 146,893 and 146,892 as well as European Pat. Appln. Nos. 88100799.1 and 88100801.5, respectively).

Since each of the antibacterial polypeptides produced by the insect of *Sarcophaga peregrina* or obtained through cultivation of the cell line shows a relatively wide antibacterial spectrum, almost no toxicity and is one of proteins, the substance has been expected as one of edible antibiotics and also expected as one of antitumour or anti-virus substance, but a process for preparing the polypeptides has a problem that a shift of its, laboratorical production to industrial mass-production accompanies remarkable difficulty.

SUMMARY OF THE INVENTION

A basic target of the invention, therefore, is to approach to an industrially acceptable process for obtaining the antibacterial polypeptides and its related substances, by studying and investigating the previous processes from view point of so-called—Bio-Technology—.

A primary object of the invention is to provide a cloned single- and double-stranded DNA of the antibacterial polypeptide precursor to be produced by a cell line established from *Sarcophaga peregrina* embryo, and a fragment of the DNA.

A secondary object of the invention is to provide a process for the preparation of the cloned double-stranded DNA and a fragment thereof as well as corresponding single stranded DNA.

A tertiary object of the invention is to provide a plasmid, in which the cloned double-stranded DNA or a fragment thereof is inserted, to make possible a production of the precursor or any other biologically active substance in a microorganisms or eucaryotic cell.

The present inventors have carefully and energetically studied and investigated to finally reach a novel cloned DNA of an antibacterial polypeptide precursor, and then a structure thereof has been determined to attain the basic target.

According to the present invention, the primary object can be attained by the cloned single-stranded DNA comprising about 280 nucleotides which encode the antibacterial polypeptide precursor, or a cloned double-stranded DNA consisting of said single-stranded DNA and its complementary single-stranded DNA.

The DNA according to the invention has the following nucleotide sequence or any other nucleotide sequence same with the former in biological view point.

```
5'-ATG AAA TCC TTC ATC GTA CTC GCT CTT
   ACC TTG TGC TTG GCT GCC TTC TTT ATG GGT
   CAA TCC GTA GCC TCG CCT GCT GCA GCT GCT
   GAG GAA TCT AAA TTT GTT GAT GGT TTG CAT
   GCC TTA AAA ACT ATT GAA CCG GAA TTG CAT
   GGC CGC TAC AAG AGA GCC ACT TGC GAT TTA
   TTG AGT GGC ACT GGC ATC AAT CAC TCG GCT
   TGT GCT GCC CAT TGC TTG TTG AGA GGA AAT
   CGT GGC GGC TAT TGC AAT GGC AAA GCT GTC
   TGC GTA TGT CGC AAT-3'
``` wherein A, C, G and T are, respectively, a deoxyribonucleotide having adenine, cytosine, guanine or thymine base and said sequence is given as that of each codon corresponding to a specified amino acid.

The term of—Nucleotide sequence same in biological view point—means a case of that even if, kinds or arrangement of nucleotides constituting codons, as—T-TA—and—CTG—are different but each of the codons designates same amino acid (in this case, both codons designate—leucine—). In this case, therefore, the term means nucleotide sequence encoding following amino acid sequence which is designated by said nucleotide sequence formula.

Met—Lys—Ser—Phe—Ile—Val—Leu—Ala—Val—Thr—
Leu—Cys—Leu—Ala—Ala—Phe—Phe—Met—Gly—Gln—
Ser—Val—Ala—Ser—Pro—Ala—Ala—Ala—Ala—Glu—
Glu—Ser—Lys—Phe—Val—Asp—Gly—Leu—His—Ala—
Leu—Lys—Thr—Ile—Glu—Pro—Glu—Leu—His—Gly—
Arg—Tyr—Lys—Arg—Ala—Thr—Cys—Asp—Leu—Leu—
Ser—Gly—Thr—Gly—Ile—Asn—His—Ser—Ala—Cys—
Ala—Ala—His—Cys—Leu—Leu—Arg—Gly—Asn—Arg—
Gly—Gly—Tyr—Cys—Asn—Gly—Lys—Ala—Val—Cys—
Val—Cys—Arg—Asn

According to a process of the invention, the cloned double-stranded DNA encoding the antibacterial polypeptide precursor can be prepared by converting RNA obtained from a cell line to be established from *Sarcophaga peregrina* embryo, into poly(A)RNA, constructing cDNA library with use of the poly(A)RNA and vector/primer DNA to carry out a transformation of *Esherichia coli* (*E. coli*), while, previously synthesizing a mixture of 16 heptadecamers, each consisting of 17 deoxyribonucleotides of the formula

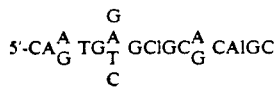

wherein I is inosine, which is complementary to mRNA corresponding to

Ala-Cys-Ala-Ala-His-Cys of 15th to 20th amino acids from N-terminal in known amino acid sequence for an antibacterial polypeptide obtained from a cell line to be established from *Sarcophaga peregrina* embryo and a mixture of 16 eicosamers, each consisting of 20 deoxyribonucleotides of the formula

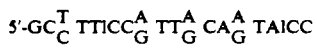

wherein I is inosine, which is complementary to mRNA corresponding to

Gly-Tyr-Cys-Asn-Gly-Lys-Ala of 28th to 34th amino acids from N-terminal in the known amino acid sequence for the antibacterial polypeptide, labeling each synthesized oligodeoxyribonucleotide shown by said formulae (A) and (B) at 5'-terminal, screening said transformed *E. coli* by a hybridization using said labeled oligodeoxyribonucleotides as probes to obtain a positive clone which hybridizes to both of the probes.

The ground that the 15th to 20th amino acids from N-terminal in amino acids for the known antibacterial polypeptide is selected for the oligodeoxyribonucleotide (A) as one of the probes and that the 28th to 34th amino acids from N-terminal in amino acids for the known antibacterial polypeptide is selected for the oligodeoxyribonucleotide (B) as the other probe lies in making possible to respond for 6 or 7 polypeptides sequence and minimize kinds of oligodeoxyribonucleotide corresponding to such amino acids by suitably using inosine. In the screening of transformed cell (*E. coli*), there is no difference in result, even if the hybridization with the oligodeoxyribonucleotides (A) is carried out prior to that with the other oligodeoxyribonucleotides (B), or vise versa.

A cloned single-stranded DNA encoding the antibacterial polypeptide precursor can be prepared by separating the resulting cloned double-stranded DNA with use of a method known per se, for instance treating at 90° C. for about 3 minutes and then cooling same with an ice bath.

The cloned single or double-stranded DNA encoding the antibacterial polypeptide precursor can be made into fragments of various length, by treating with a suitable restriction enzyme(s), binding fragments, synthesizing a region not obtaining a cleaving technique and binding the synthesized region to the fragment.

The cloned double-strand DNA encoding the antibacterial polypeptide precursor region or any fragment thereof may be inserted into a plasmid with a technique known per se, for instance taking out a plasmid from *E. coli*, purifying the plasmid, treating the plasmid with a restriction enzyme to cut the plasmid at a specified base position, and ligating with a DNA ligase the cloned DNA to the cleavage of the cut plasmid to re-construct a plasmid with the recombinant DNA.

If a microorganism or an eucaryotic cell is transformed with the plasmid which incorporates the double-strand DNA or a fragment thereof according to the invention and cultivated the microorganism or eucaryotic cell, the antibacterial polypeptide precursor, antibacterial polypeptide per se or other biologically active substances can be prepared in a large amount.

BRIEF DESCRIPTION OF THE DRAWING

FIG. 2 shows a determined nucleotide sequence of the cloned cDNA encoding the antibacterial polypeptide precursor as well as an amino acid sequence corresponding to the nucleotide sequence in the antibacterial polypeptide region.

PREFERRED EMBODIMENTS OF THE INVENTION

Figure 1:
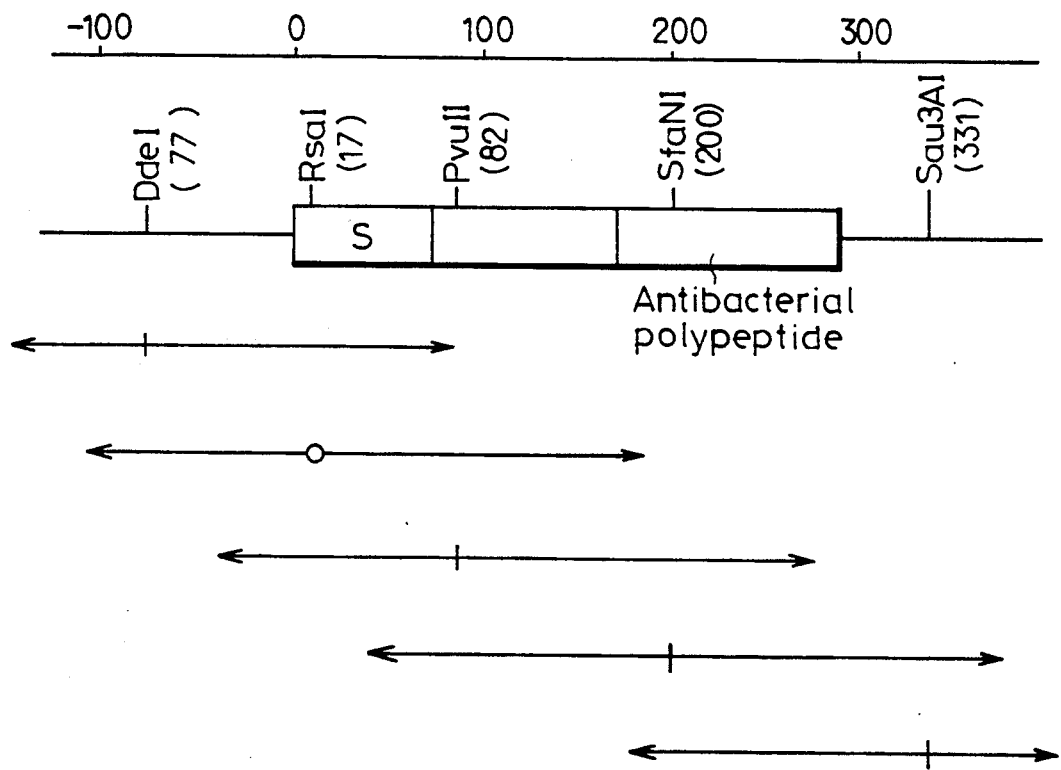
FIG. 1 is a strategy for sequencing cloned cDNA encoding the antibacterial polypeptide precursor according to the invention and a restriction enzyme map which displays only relevant restriction endonuclease sites.

The invention will now be further explained with reference to Examples and a Test Example for determining a structure of a cloned DNA encoding an antibacterial polypeptide precursor.

EXAMPLE 1 a) Preparation of Poly(A)RNA Comprising mRNA of Antibacterial Polypeptide

An antibacterial polypeptide containing 6 cysteine residues has been obtained and purified from culture supernatant of a cell line (NIH-Sape-4) established from *Sarcophaga peregrina* embryo and its structure has already been determined as disclosed in the specification for Jap. Pat. Appln. No. 14807/1987 corresponding to U.S. Pat. application Ser. No. 146,892 and Eurpean Pat. application No. 88100801.1. Therefore, the NIH-Sape-4 cells were treated, in accordance with the method as disclosed by Chirgwin, J. M. et al ["Biochemistry" Vol. 18, pages 5294–5299 (1979)]. Namely, the total RNA (1.2 mg) was extracted from the cells of $5 \times 10^8$ by guanidium thiocyanate, bound to an oligo(dT)cellulose column with use of 10 mM-Tris hydrochloride buffer containing 0.5M KCl, as a binding buffer, and eluted with use of a similar buffer but free from KCl to obtain poly(A)RNA (150 μg).

b) Construction of cDNA Library

A cDNA (plasmid) library was constructed with use of 30 μg of said poly(A)RNA and 4.3 μg of vector/primer DNA and in accordance with the method disclosed by Okayama, H. and Berg, P. ["Mol. Cell. Biol." Vol. 2, pages 161–170 (1982)] and *E. coli* (HB101) was transformed in accordance with the method disclosed by Morrison, D. A. ["Methods in Enzymol." Vol. 68, pages 326–331 (1979)]. Through a screening with use of LB-agar plate containing 50 μg/ml of ampicillin, ampicillin resistant transformants were obtained by 10000 cells per 1 μg of poly(A)RNA, namely about 300,000 cells in total.

(c) Synthesis of oligodeoxyribonucleotides complementary to mRNA corresponding to amino acid sequence for antibacterial polypeptide obtained from supernatant liquid on cultivation of NIH-Sape-4

A mixture of 16 heptadecamers, each consisting of 17 deoxyribonucleotides of the formula

wherein I is inosine, which is complementary to mRNA corresponding to

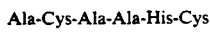

of the 15th to 20th amino acids from N-terminal in the known amino acid sequence for the antibacterial polypeptide obtained from culture supernatant of NIH-Sape-4 and a mixture of 16 eicosamers, each consisting of 20 deoxyribonucleotides of the formula

wherein I is inosine, which is complementary to mRNA corresponding to

of the 28th to 34th amino acids from N-terminal in the known amino acid sequence for the antibacterial polypeptide obtained from culture supernatant of NIH-Sape-4 were synthesized with use of DNA synthesizer marketed by Pharmacia AB and in accordance with β-cyanoethylphosphamidide method ["Nucleic Acids Res." Vol. 16, pages 257–260 (1958)].

(d) Cloning

The cloning was carried out in accordance with the method as disclosed by Hanahan, D. et al ["Gene" Vol. 10, pages 63–67 (1980)].

Namely, about 20000 cells among said about 300,000 ampicillin resistant transformants as described in said item (b) were replicated on nitrocellulose filter, cultivated for 3 to 4 hours on a agar plate containing 50 μg of ampicillin and transferred on LB-agar plate containing 500 μg of chloramphenicol to further cultivate the same at 37° C. for one overnight. A colony formed on the filter was subjected to a bacteriolysis in 0.5N NaOH for 5 minutes, namely a double-strand DNA was made into a single-strand DNA, fixed on a plate, neutralized in 1N Tris-hydrochloride buffer (pH 7.5) for 5 minutes, and dipped the filter for 5 minutes in 1M Tris-hydrochloride buffer (pH 7.5) containing 1.5M-NaCl to remove bacterial fragments and the like other than DNA. Thereafter, the filter was air dried and baked for 2 hours at 80° C. to obtain a testing filter for screening, which is nitrocellulose filter carrying DNA of about 20000 transformants.

While, the screening of the transformants was carried out as follows, in accordance with the method as disclosed by Grunstein, M. et al ["Proc. Natl. Acad. Sci. U.S.A." Vol. 72, pages 3961–3965 (1975)].

Each of the oligodeoxyribonucleotides synthesized by the method as stated in said item (c) and shown by said formulae A and B was end-labeled at 5′-terminal with [γ-$^{32}$P]ATP (Amersham, 5000 Ci/mmol) and T$_4$ polynucleotide kinase (Toyobo Co. Ltd., Osaka, Japan) to make the oligodeoxyribonucleotides into probes for screening. A relative activity of each probe was 1 to $2 \times 10^7$ cpm/pmol.

The transformants on the testing filter were screened by a hybridization at 43° C. and with use of the labeled oligodeoxyribonucleotides of the group shown by the Formula A, as the probes and judged by the autoradiogram method, and by also another hybridization at 45° C. and with use of the labeled oligodeoxyribonucleotides of the group shown by the Formula B, as the other probes and judged by the autoradiogram method, to find that only 12 transformants among about 20,000 transformants are positive clones hybridizable to both oligodeoxyribonucleotide groups A and B.

These positive clones were then analyzed by an electrophoresis to find that those have a cDNA insert region of about 500 bp including poly(dA)(dT) tails and poly(dG)(dC) tracts. The cloned DNA is double-stranded one and nucleotide sequence thereof was elucidated as stated in the Test Example as given later. Therefore, the DNA can be made into a fragment(s) in various length, by treating same with a suitable restriction enzyme(s) and if necessary, binding a synthetic DNA to the fragment to obtain a desired DNA fragment having the antibacterial polypeptide precursor region, antibacterial polypeptide region or other region showing a certain biological activity.

The double-stranded DNA and its fragment or piece can be made into corresponding single-stranded one by treating same at 90° C. for about 3 minutes and then ice cooling to cause a separation thereof.

Further, the double-stranded DNA or its fragment may be inserted into a plasmid, in accordance with conventional techniques, for instance by taking out the plasmid from E. coli or the like, purifying same, treating the plasmid with restriction enzyme(s) to cut the plasmid at specified base positions, and ligating with DNA ligase(s) the cloned DNA or its fragment to the cleavages of the cut plasmid to re-construct a plasmid with the recombinant DNA. A microorganism or eucaryotic cell can be transformed with such DNA recombinant plasmid in a conventional manner and cultivated to produce the antibacterial polypeptide precursor, antibacterial polypeptide per se or other biologically active substances.

TEST EXAMPLE

Determination of Nucleotide Sequence for Cloned Antibacterial Polypeptide Precursor and Corresponding Amino Acid Sequence A nucleotide sequence of cDNA insert region for the cloned antibacterial polypeptide precursor was determined directly or by sub-cloning to a pUC19 plasmid, in accordance with the method disclosed by Maxam, A. M. et al ["Methods in Enzymol." Vol. 65, pages 499–560 (1980)] and the method disclosed by Hattori, M. et al ["Anal. Biochem" Vol. 152, pages 232–238 (1980)] who employ a modified plasmid.

In FIG. 1, there are given a cDNA region of the antibacterial polypeptide precursor containing clone, restriction enzymes selected for determining the nucleotide sequence in the region and a strategy for sequencing the cloned cDNA. The numerals at uppermost portion in the Figure are nucleotide number given as from the antibacterial polypeptide precursor region boxed at intermediate portion. The —PvuII—and the like are names of restriction enzymes and a numeral given in parentheses shows a cleavage portion or starting position (nucleotide number) for determining the nucleotide sequence. Among the boxed region for antibacterial polypeptide precursor, a region (S) shows that to be a signal peptides, and the antibacterial polypeptide region lies at C-terminal site in the precursor region and in N-terminal site, there are two basic amino acids (Lys-Arg). In the lower portion in FIG. 1, each of horizontal arrows shows a direction and limit of the nucleotide sequence to be determined, due to the respective restriction enzyme. Each of the determination results carried out according to the method disclosed by Maxam, A. M. et al is shown by an arrow with a short vertical line which shows an isotope labeled position at 5'-terminal. While, each determination result carried out by the dideoxy method disclosed by Hattori, M. et al is shown by adding a small circle at an end of the arrow which indicates a starting position for nucleotide sequencing.

In FIG. 2, there are shown thus determined nucleotide sequence of the cloned cDNA encoding the antibacterial polypeptide precursor as well as the amino acid sequence corresponding to the nucleotide sequence in the antibacterial polypeptide precursor region. In FIG. 2, the numeral given at upper side is the number of nucleotides as in FIG. 1, and another numeral given at lower side is number of amino acid residues in the antibacterial polypeptide precursor region, which number begins from the initiating methionine (Met) in the open reading frame in the precursor region. The region boxed with a solid line shows the cloned antibacterial polypeptide region.

The antibacterial polypeptide precursor region lies as the long open reading frame intiating from the initiation codon of ATG and terminating at the termination codon of TAA. In the precursor region, there is the nucleotide sequence encoding amino acid sequence for the antibacterial polypeptide previously determined by one of the present inventors and containing 6 cysteines, which lies in the region from alanine (Ala) in the 55th position of the amino acid number initiating from methionine (Met) to asparagine (Asn) in the 94th position thereof, just before the termination codon of TAA.

The N-terminal region of the antibacterial polypeptide precursor, namely the underlined 1st Met to 23rd Ala seems to be a signal sequence (S region in FIG. 1) which may generally be found on secretory proteins, in view of its structure consisting of relative hydrophobic amino acids. Near the 3'-terminal, there is the nucleotide sequence of AATAA (region of nucleotide Nos. 324–329) which is usually located in upper stream of poly(A) sequence in eucaryotic mRNA.

EXAMPLE 2

Preparation of Plasmid Integrating the Antibacterial Polypeptide Precursor

This embodiment will be explained with reference to the drawings and more particularly FIG. 3. In the first place, the cDNA clone of antibacterial polypeptide precursor as shown in FIGS. 1 and 2 was treated with restriction enzymes of SfaNI and Sau3AI to obtain a fragment of about 130 bp. On the other hand, an EcoRI linker was prepared with use of a DNA synthesizer marketed by Pharmacia AB. The linker was joined to SfaNI cleavage of the fragment, whereby DNA fragment encoding the amino acid sequence for the desired antibacterial polypeptide can be prepared.

While, a commercially available plasmid (—pUC1-8—marketed by Pharmacia AB) was treated with the restriction enzymes of EcoRI and BamHI. To the resulting ends, said fragment with linkers was joined to re-construct into a plasmid, in which the antibacterial polypeptide is inserted.

Figure 3:
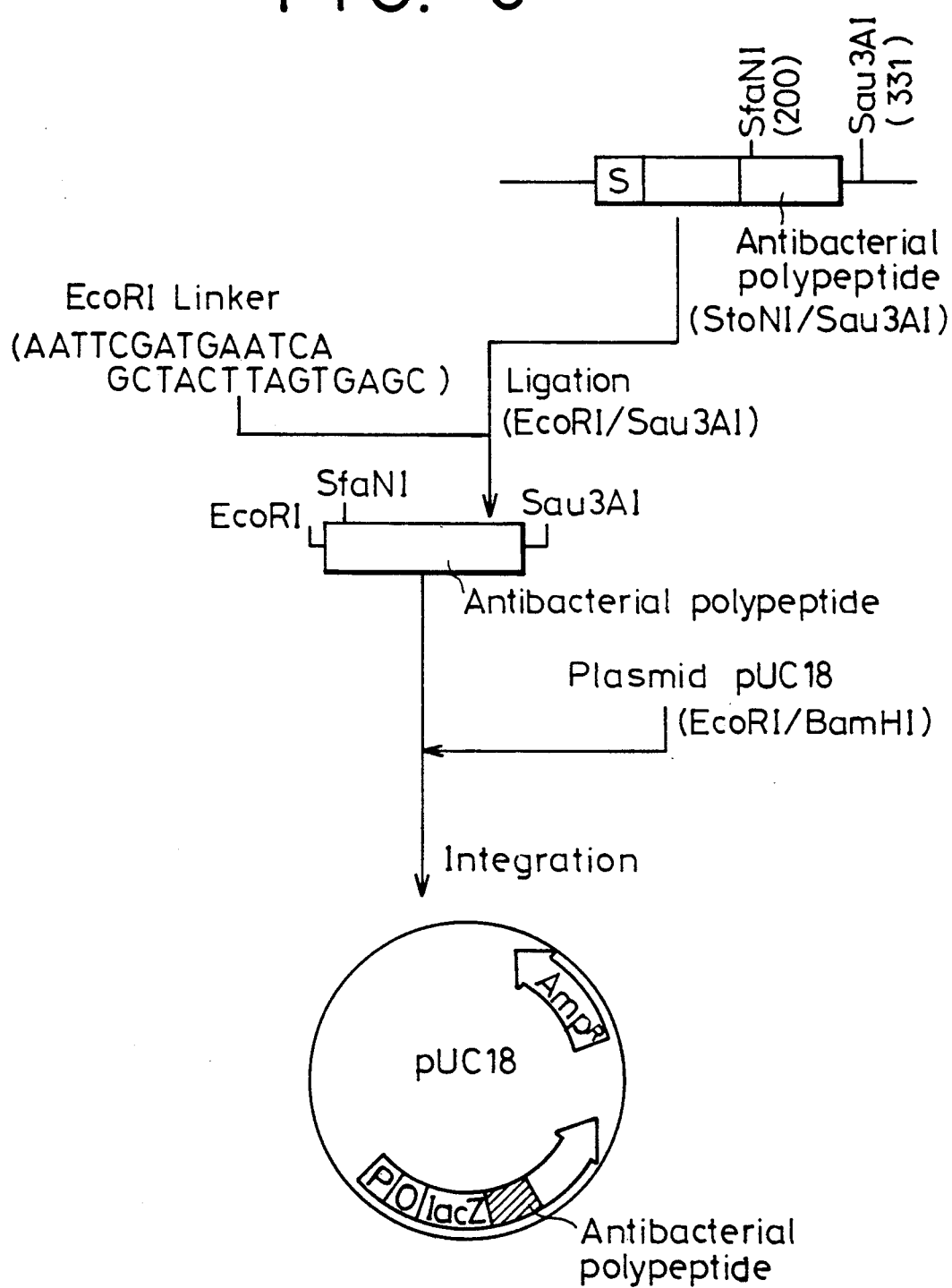
FIG. 3 illustrates steps for preparing a plasmid, wherein the cloned DNA encoding the antibacterial polypeptide is inserted.

As shown in the last portion in FIG. 3, the resulting plasmid has the cDNA clone of the antibacterial polypeptide joined through Met to a part of a structural lacZ protein at down stream of lac promoter.

The plasmid with such recombinant DNA can be transferred into E. coli or the like, in a conventional manner, to produce the biological active substance in a large amount, and the desired antibacterial polypeptide therein can be obtained by cleaning with cyanogen bromide at the position of Met to make its large scale production possible.

What is claimed is:

1. An isolated and purified DNA sequence which encodes an antibacterial polypeptide precursor and which has the following nucleotide sequence

```
5'-ATG AAA TCC TTC ATC GTA CTC GCT GTT
ACC TTG TGC TTG GCT GCC TTC TTT ATG GGT
CAA TCC GTA GCC TCG CCT GCT GCA GCT GCT
GAG GAA TCT AAA TTT GTT GAT GGT TTG CAT
GCC TTA AAA ACT ATT GAA CCG GAA TTG CAT
GGC CGC TAC AAG AGA GCC ACT TGC GAT TTA
TTG AGT GGC ACT GGC ATC AAT CAC TCG GCT
TGT GCT GCC CAT TGC TTG TTG AGA GGA AAT
CGT GGC GGC TAT TGC AAT GGC AAA GCT GTC
TGC GTA TGT CGC AAT -3'
```

2. An isolated and purified DNA sequence which encodes the following amino acid sequence

```
Met—Lys—Ser—Phe—Ile—Val—Leu—Ala—Val—Thr—
Leu—Cys—Leu—Ala—Ala—Phe—Phe—Met—Gly—Gln—
Ser—Val—Ala—Ser—Pro—Ala—Ala—Ala—Ala—Glu—
Glu—Ser—Lys—Phe—Val—Asp—Gly—Leu—His—Ala—
Leu—Lys—Thr—Ile—Glu—Pro—Glu—Leu—His—Gly—
Arg—Tyr—Lys—Arg—Ala—Thr—Cys—Asp—Leu—Leu—
Ser—Gly—Thr—Gly—Ile—Asn—His—Ser—Ala—Cys—
Ala—Ala—His—Cys—Leu—Leu—Arg—Gly—Asn—Arg—
Gly—Gly—Tyr—Cys—Asn—Gly—Lys—Ala—Val—Cys—
Val—Cys—Arg—Asn.
```

3. A plasmid comprising the DNA sequence of claim 1.

4. A process for the preparation of the DNA sequence of claim 1, which process comprises
isolating poly(A)RNA from a Sarcophaga peregrina cell line;
constructing a cDNA library with the poly(A)RNA;
screening a cDNA library with a mixture of synthetic oligonucleotides selected from the group consisting of

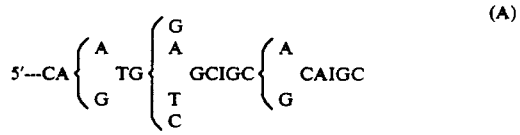

(A)

wherein I is inosine, and the formula

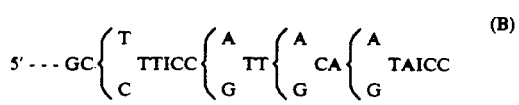

(B)

wherein I is inosine; and isolating cDNA clones which hybridize to said synthetic oligonucleotides.

* * * * *